Figure 1:
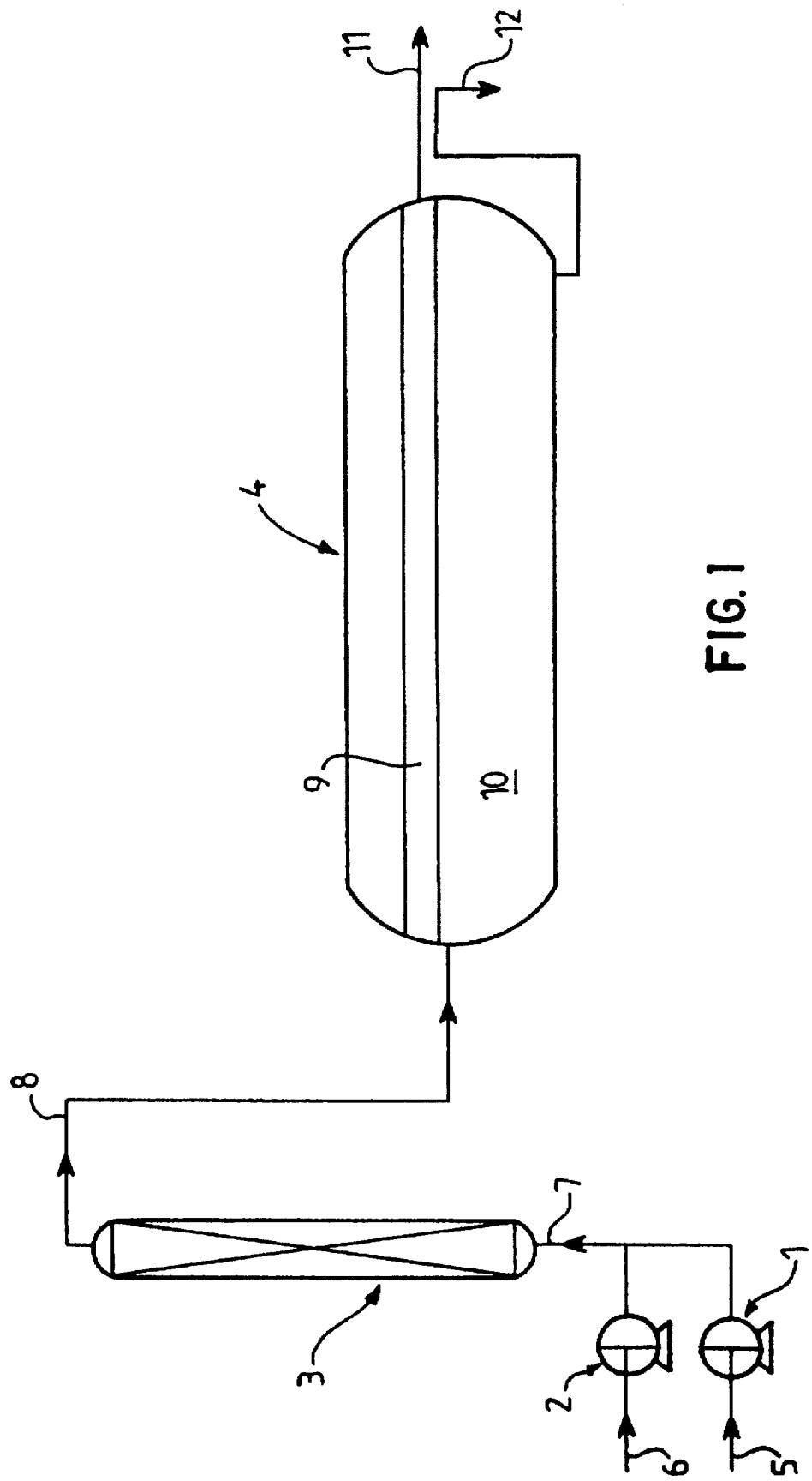

United States Patent [19]
Ollivier et al.

[11] Patent Number: 5,801,283
[45] Date of Patent: Sep. 1, 1998

[54] PROCESS FOR THE PURIFICATION OF AN ALKANESULPHONYL CHLORIDE AND OF THE CORRESPONDING ALKANESULPHONIC ACID

[75] Inventors: Jean Ollivier, Arudy; Annie Commarieu, Pau, both of France

[73] Assignee: Elf Atochem S.A., France

[21] Appl. No.: 842,396

[22] Filed: Apr. 24, 1997

[30] Foreign Application Priority Data

Apr. 24, 1996 [FR] France ................... 96 05170

[51] Int. Cl.⁶ ................................................. C07C 143/70
[52] U.S. Cl. ................................................. 562/828
[58] Field of Search ................................. 562/828

[56] References Cited

U.S. PATENT DOCUMENTS 4,549,993  10/1985  McElligott, Jr. .
4,876,048  10/1989  Gardner et al. .
4,938,846  7/1990  Comstock et al. .

FOREIGN PATENT DOCUMENTS 373 304 A1  6/1990  European Pat. Off. .
373 304 B1  6/1990  European Pat. Off. .
C-1103323   4/1959  Germany .
C-1119855   9/1960  Germany .

*Primary Examiner*—Paul J. Killos
*Attorney, Agent, or Firm*—Bell, Boyd & Lloyd

[57] ABSTRACT

The process for the purification of an alkanesulphonyl chloride (ASC) in order to reduce the sulphate content thereof consists in washing the alkanesulphonyl chloride with water or with an aqueous solution of an acid having a pH of between −0.57 and 7 and then in separating the alkanesulphonyl chloride thus purified from the aqueous phase.

This purified ASC leads, by total hydrolysis, to alkanesulphonic acid with a low content of sulphuric acid.

10 Claims, 1 Drawing Sheet

PROCESS FOR THE PURIFICATION OF AN ALKANESULPHONYL CHLORIDE AND OF THE CORRESPONDING ALKANESULPHONIC ACID

FIELD OF THE INVENTION

The present invention relates to the purification of an alkanesulphonyl chloride (ASC). The aim of the invention is more particularly to reduce considerably the content of sulphuric acid contained in the alkanesulphonic acid (ASA) subsequently obtained by hydrolysis of the said alkanesulphonyl chloride.

BACKGROUND OF THE INVENTION

The term "alkane" is understood to refer to lower alkane radicals having a carbon number ranging from 1 to 4, in particular methyl, ethyl, n-propyl and n-butyl radicals.

It is known that for electrochemical applications, or for applications in the surface treatment of methanesulphonic acid, the presence of sulphuric acid is to be avoided. The reason for this is that, in the presence of lead, lead sulphate may precipitate and limit the performance of the methanesulphonic acid. The commercial specification for this type of application of methanesulphonic acid is moreover such that the content of sulphuric acid must be less than 350 ppm.

It is already known to purify methanesulphonic acid by precipitation or by distillation.

In the precipitation method, the fact that lead sulphate and barium sulphate are insoluble in methanesulphonic acid is used; however, the lead or the barium which remains in the methanesulphonic acid after the treatment are undesirable contaminants.

In the distillation method, the fact that the boiling point of sulphuric acid is higher than that of methanesulphonic acid is used. Since this involves removing traces of sulphuric acid in the methanesulphonic acid, the methanesulphonic acid would in fact have to be distilled from the methanesulphonic acid/sulphuric acid mixture. Not only is this solution economically uninteresting, but it also requires specific apparatus (cf. U.S. Pat. No. 4,938,846) in order to avoid the thermal degradation of the methanesulphonic acid. Practice shows that it is difficult to pass below 1000 ppm of sulphuric acid in methanesulphonic acid, whereas the specification is 350 ppm of sulphuric acid for methanesulphonic acid at a concentration of 70% by weight in water.

Moreover, U.S. Pat. No. 4,549,993 teaches a process for the purification of alkanesulphonyl chloride by washing with an aqueous hydrochloric acid solution containing at least about 18% by weight of HCl relative to the weight of the solution, and then by rectifying the alkanesulphonyl chloride separated from the aqueous solution at a temperature not above about 70° C., under a reduced pressure not greater than 500 torr and while flushing with an inert gas. Preferably, the HCl concentration is from 30 to 36% by weight in order to reduce significantly the hydrolysis of the methanesulphonyl chloride (MSC), the technical aim being to obtain MSC free of methanesulphonic acid, the problem of the sulphates and in particular of the sulphuric acid not being addressed.

BACKGROUND DESCRIPTION OF THE DRAWINGS

The FIGURE depicts a flow diagram which is not considered to limit the invention.

DESCRIPTION OF THE INVENTION

Applicant has now found that the problem of the presence of sulphuric acid in alkanesulphonic acid (ASA) can be solved by treating the alkanesulphonyl chlorides (ASC) with water or with an aqueous solution of an acid having a pH of between −0.57 and 7, which leads to a purified ASC, it being possible for the latter to be collected as an intermediate product before being subjected to total hydrolysis with water at high temperature to give the purified alkanesulphonic acid (ASA).

In the remainder of the account, sulphate refers to any compound which is present as an impurity in the alkanesulphonyl chloride and which, in the presence of water, leads to sulphuric acid $2H^+$ $SO_4^{2-}$, $SO_4^{2-}$ compounds, countercations, sulphuric acid itself and sulphuric acid precursors such as, in particular, sulphuryl chloride, $SO_3$, and $C_1$ to $C_4$ lower alkyl esters of chlorosulphonic acid, for example, fall within the scope of this definition.

The subject of the present invention is thus, firstly, a process for the purification of an alkanesulphonyl chloride (ASC), in order to reduce the sulphate content thereof, characterized in that the said chloride is treated by placing it in contact with a washing liquid chosen from water or an aqueous solution of an acid having a pH between −0.57 and 7, and then by separating the alkanesulphonyl chloride from the washing liquid, the latter having dissolved most of the sulphates, thereby causing a decrease in the sulphate content of the treated alkanesulphonyl chloride, which is, in this way, purified.

Preferably, the water has a pH of about 7 or alternatively the aqueous solution of an acid has a pH in the region of 7. This is, for example, the case with water which has dissolved carbon dioxide ($CO_2$) present in the ambient air or alternatively water containing traces of an acid. The reason for this is that it is with such washing liquids that the greatest decrease in sulphates is observed.

Advantageously, the alkanesulphonyl chloride is chosen from methanesulphonyl chloride (MSC), ethanesulphonyl chloride (ESC), n-propanesulphonyl chloride (PSC) and n-butanesulphonyl chloride (BSC).

Treatment of this alkanesulphonyl chloride according to the process of the present invention may be carried out in a batchwise or continuous manner. According to the technological solution adopted, vigorous mechanical stirring may be used, for example, in order for the alkanesulphonyl chloride and the water or the aqueous solution, which are essentially immiscible, to be placed in intimate contact, or alternatively a static mixer system such as a vertical column may be used.

In the case of a batchwise treatment, the ASC/water or ASC/aqueous solution mixture is stirred vigorously in order momentarily to increase the surface area of contact at the interface of the two immiscible liquid phases.

Advantageously, the duration of this stirring may be chosen to be between a few seconds and 1 hour depending on the temperature of the medium stirred, and preferably from 3 to 5 minutes, at a temperature of 20° C. At the end of the stirring, the phases are allowed to separate out by settling and the organic phase consisting of the purified ASC is recovered.

In the case of a continuous treatment, the apparatus comprises a mixer which ensures the placing in contact of the ASC/water or ASC/aqueous solution and a decanter of a size such that it allows the organic phase and the aqueous phase to separate.

Advantageously, the washing liquid is used in an amount by weight ranging from 1% to 50% of the weight of the ASC to be purified. Preferably, the amount of washing liquid is from 3% to 7% of the weight of the ASC to be purified.

Advantageously, the placing in contact of the washing liquid/ASC takes place at a phase temperature ranging from 0° C. to 50° C.

This temperature is preferably from 10° C. to 20° C. so as not to incur high operating costs or to give rise to any appreciable hydrolysis of the ASC.

Advantageously, the aqueous solution of an acid comprises hydrochloric acid at a content by weight of less than 18% relative to the total weight of this aqueous solution, thereby ensuring a pH about −0.57 and below 7.

The subject of the present invention is also a process for the manufacture of alkanesulphonic acid with a low content of sulphuric acid, characterized in that total hydrolysis is carried out on the alkanesulphonyl chloride purified beforehand according to the above process with its optional variants.

The alkanesulphonic acid (ASA) with a low content of sulphuric acid may in particular be methanesulphonic acid (MSA), ethanesulphonic acid (ESA), n-propanesulphonic acid (PSA) or n-butanesulphonic acid (BSA).

EXAMPLES

In addition to the preceding description, the examples which follow illustrate the present invention with, in particular, the single FIGURE which schematically represents apparatus designed to carry out the process for the continuous purification of an ASC.

EXPERIMENTAL SECTION

The sulphate content in the ASCs comprises the sulphate anion itself $SO_4^{2-}$ as well as any precursor which leads to the sulphate anion $SO_4^{2-}$ by hydrolysis. The sulphate content is always relative to the weight of $SO_4^{2-}$ obtained after total hydrolysis of the initial ASC and after total hydrolysis of the purified ASC. The hydrolyses are performed at the boiling point of a water (20 g)/ASC (0.5 g) mixture for at least 3 minutes.

The difference in values between these two contents shows the efficacy of the purification by contact with the washing liquid.

The content of sulphate ions $SO_4^{2-}$ is measured by gravimetric analysis or by ionic chromatography of samples of alkanesulphonic acids obtained by total hydrolysis.

EXAMPLES 1 AND 2

MSC and 5 or 10% by weight of double-deionized water (pure water containing no ions with a total concentration of greater than or equal to 0.5 ppm), relative to the total weight of the MSC/water mixture, are introduced, at a temperature of 20° C., into a separating funnel and the mixture is shaken vigorously for 3 minutes. After separation of the phases by settling over a period of 24 hours, the MSC and aqueous phases are collected, weighed and analysed.

The results obtained are featured in Table I below.

TABLE I

|  |  | EXAMPLE 1 | EXAMPLE 2 |
|---|---|---|---|
| Initial MSC | Mass in g | 95 | 90 |
|  | $SO_4^{2-}$ ppm | 815 | 815 |
| Double-deionized pure water | Mass in g | 5 | 10 |
|  | $SO_4^{2-}$ in ppm | <0.5 | <0.5 |

TABLE I-continued

|  |  | EXAMPLE 1 | EXAMPLE 2 |
|---|---|---|---|
| Final MSC | Mass in g | 97.3 | 92.7 |
|  | $SO_4^{2-}$ ppm | 42 | 41 |
| Final aqueous phase | Mass in g | 3.2 | 8.7 |
|  | $SO_4^{2-}$ in ppm | 1160 | 520 |

COMPARATIVE EXAMPLE 3

The procedure is identical to that of Example 1, except that the 5 g of pure water are replaced by 5 g of 33% by weight HCl having a sulphate content of less than 8 ppm, this value measured by the above methods.

After separation of the aqueous phase and the MSC phase by settling over a period of 5 hours, the MSC phase has an $SO_4^{2-}$ content of 183 ppm relative to the MSC.

If the period of separation by settling is extended to 24 hours, the $SO_4^{2-}$ content relative to the MSC falls to 130 ppm.

COMPARATIVE EXAMPLE 4

The procedure is identical to that of Example 1, except that the 5 g of water are replaced by 5 g of 18% HCl having a sulphate content of less than 8 ppm.

After separation by settling for a period of 5 hours, the purified MSC contains 342 ppm of $SO_4^{2-}$ relative to the MSC.

After separation by settling for 24 hours, this content falls to 135 ppm.

EXAMPLE 5

The procedure is identical to that of Comparative Example 3 or 4, except that the 33% or 18% HCl is replaced by 10% by weight HCl with a sulphate content of less than 8 ppm.

After separation by settling for a period of 5 hours, the purified MSC contains 111 ppm of $SO_4^{2-}$ relative to the MSC.

After separation by settling for 24 hours, this content falls to 100 ppm.

Examples 1 to 5 show that water leads to a better result since it leads to a lower residual content of sulphates than does 10%, 18% or 33% HCl.

10% HCl leads to slightly better results than those obtained with 18 or 33% HCl.

EXAMPLE 6

The treatment is performed in a batchwise manner.

100 g of MSC containing 950 ppm of sulphates relative to an $SO_4^{2-}$ weight equivalent are introduced into a separating funnel with 5 g of distilled water. The mixture is then shaken vigorously for 30 seconds and the phases are then left to separate by settling over 5 hours. At the end of this period, the MSC is separated from the aqueous phase and then analysed in the usual manner. The final $SO_4^{2-}$ content in the MSC, relative to the MSC, is 40 ppm.

EXAMPLE 7

The procedure is identical to Example 1, except that the MSC is replaced by ethanesulphonyl chloride (ESC) initially containing 432 ppm of sulphates, calculated as an $SO_4^{2-}$ weight equivalent.

After separation of the phases by settling over a period of 24 hours, the purified ESC shows a final $SO_4^{2-}$ content, relative to the ESC, of 30 ppm.

EXAMPLE 8

The procedure is identical to that of Example 1, except that the MSC is replaced by propanesulphonyl chloride (PSC) initially containing 650 ppm of sulphates, calculated as an $SO_4^{2-}$ weight equivalent.

After separation of the phases by settling over a period of 24 hours, the PSC shows a final $SO_4^{2-}$ content, relative to the PSC, of 25 ppm.

EXAMPLES 9 TO 14

The treatment is performed continuously in the apparatus represented in the single figure. This apparatus includes a metering pump 1 for supplying water 5 and a metering pump 1 for supplying MSC 6 with a common pipe 7 emerging at the foot of a vertical column 3 which acts as a static mixer. This column 3 is 400 mm in height for an inside diameter of 10 mm (useful volume of 19 ml) and is packed with glass rings 4 mm in outside diameter. The mixture of MSC and aqueous phase leaves at the top of the column via the pipe 8 which emerges into one of the two side ends of a tubular horizontal decanter 4 350 mm long and 100 mm in inside diameter. The aqueous phase 9 and the MSC are maintained at a constant level in the decanter 4 by means of a pipe 11 for removal of the aqueous phase, which emerges at the other end of the decanter 4, and by a pipe 12 for removal of the purified MSC, which emerges onto the lower base of the decanter for withdrawal of the MSC, which is denser than the aqueous phase.

The residence times of the MSC in the decanter may range from 4.5 to 5.5 hours and that of the water from 3 to 59 hours.

The results obtained are featured in Table II below.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

TABLE II

| Examples | Initial $SO_4^{2-}$ content in the MSC (ppm) | % $H_2O$ by weight relative to the total weight of $H_2O$ and MSC | Temperature (°C.) | Residence time Mixer (min.) | Residence time MSC in the decanter (h) | Residence time Aqueous phase in the decanter (h) | Final content of $SO_4^{2-}$ in the purified MSC (ppm) |
|---|---|---|---|---|---|---|---|
| 9 | 747 | 3.5 | 19 | 15 | 5.5 | 19 | 129 |
| 10 | 950 | 4 | 19 | 4 | 5 | 59 | 114 |
| 11 | 747 | 5.9 | 30 | 4 | 4.5 | 16 | 85 |
| 12 | 403 | 7.2 | 4 | 4 | 5 | 12 | 143 |
| 13 | 950 | 9.3 | 19 | 4 | 5.5 | 25 | 126 |
| 14 | 512 | 12.2 | 19 | 3.5 | 5 | 3 | 181 |

We claim:

1. Process for the purification of an alkanesulphonyl chloride (ASC), to reduce the sulphate content thereof, comprising treating the said chloride by placing it in contact with a washing liquid selected from water or an aqueous solution of an acid having a pH of between 0.57 and 7, and then by separating the alkanesulphonyl chloride from the washing liquid, the latter having dissolved most of the sulphates, thereby causing a decrease in the sulphate content of the treated alkanesulphonyl chloride, which is, in this way, purified.

2. Process according to claim 1, wherein the water has a pH of about 7.

3. Process according to claim 1, wherein the aqueous solution of an acid has a pH in the region of 7.

4. Process according to claim 1, wherein the alkanesulphonyl chloride is selected from methanesulphonic chloride (MSC), ethanesulphonyl chloride (ESC), n-propanesulphonyl chloride (PSC) and n-butanesulphonyl chloride (BSC).

5. Process according to claim 1, wherein the washing liquid is used in an amount by weight ranging form 1% to 50% of the weight of the alkanesulphonyl chloride to be purified.

6. Process according to claim 5, wherein the said amount is from 3 to 7% of the weight of the alkanesulphonyl chloride to be purified.

7. Process according to claim 1, wherein that placing in contact of the washing liquid/alkanesulphonyl chloride takes place at a phase temperature ranging from 0° C. to 50° C.

8. Process according to claim 7, wherein the said temperature is from 10° to 20° C.

9. Process according to claim 1, wherein the aqueous solution of an acid comprises hydrochloric acid at a content by weight of less than 18% by weight relative to the total weight of this aqueous solution, thereby ensuring a pH above −0.57 and below 7.

10. Process for the manufacture of alkanesulphonic acid with a low content of sulphuric acid, with a low content of sulphuric acid, where total hydrolysis is carried out on the alkanesulphonyl chloride purified beforehand by the process of claim 1.

* * * * *